United States Patent [19]
Morales et al.

[11] Patent Number: 5,880,108
[45] Date of Patent: *Mar. 9, 1999

[54] METHOD FOR TREATING THE INTERNAL URINARY BLADDER AND ASSOCIATED STRUCTURES USING HYALURONIC ACID

[75] Inventors: Alvaro Morales, Kingston; Stanley J. Alkemade, Arva, both of Canada

[73] Assignee: Bioniche, Inc., London, Canada

[*] Notice: The term of this patent shall not extend beyond the expiration date of Pat. No. 5,591,724.

[21] Appl. No.: 824,890

[22] Filed: Mar. 26, 1997

Related U.S. Application Data

[63] Continuation-in-part of Ser. No. 644,438, May 13, 1996, which is a continuation-in-part of Ser. No. 591,015, Feb. 8, 1996, abandoned, which is a continuation-in-part of Ser. No. 388,038, Feb. 14, 1995, Pat. No. 5,591,724.

[51] Int. Cl.$^6$ .................. A61K 31/70; A61K 31/725
[52] U.S. Cl. ............................................. 514/54
[58] Field of Search ................................. 514/54

[56] References Cited

U.S. PATENT DOCUMENTS

| | | |
|---|---|---|
| 4,296,104 | 10/1981 | Herschler . |
| 4,302,577 | 11/1981 | Rucker . |
| 4,524,066 | 6/1985 | Wolf . |
| 4,640,912 | 2/1987 | Hausman . |
| 4,711,780 | 12/1987 | Fahim . |
| 4,820,693 | 4/1989 | Gillespie . |
| 4,879,282 | 11/1989 | Sablia, Jr. . |
| 4,966,890 | 10/1990 | Gillespie . |
| 5,037,810 | 8/1991 | Saliba, Jr. . |
| 5,180,715 | 1/1993 | Parsons . |

OTHER PUBLICATIONS

Stewart et al., "The Use of Dimethyl Sulfoxide (DMSO) in the Treatment of Interstitial Cystitis," *J. Urology*, vol. 98, pp. 671–672 (1968).

Parsons et al., "Decreased Urinary Uronic Acid Levels in Individuals with Interstitial Cystitis," *J. Urology*, vol. 143, pp. 690–693 (1990).

Fleischmann et al., "Clinical and Immunological Response to Nifedipine for the Treatment of Interstitial Cystitis," *J. Urology*, vol. 146, pp. 1235–1239 (1991).

Nickel et al., "The Bladder Mucus (Glycosaminoglycan) Layer in Interstitial Cystitis," *J. Urology*, vol. 149, pp.716–718 (1993).

Hanno et al., "Conservative Therapy of Interstitial Cystitial," *Seminars in Urology*, vol. 9, No. 2, pp. 143–147 (1991).

Chelsky et al., "Bladder Permeability in Interstitial Cystitis is Similar to that of Normal Volunteers: Direct Measurement by Transvesical Absorption of 99m Technetiumdiethylen-etriaminepentaacetic Acid," *J. Urology*, vol. 151, pp. 346–349 (1994).

Eldrup et al., "Permeability and Ultrastructure of Human Bladder Epithelium," *Br. J. Urology*, vol. 55, pp. 488–492 (1983).

Brandt, "The Effect of Synovial Hyaluronate on the Injection of Monosodium Urate Crystals by Leukocytes," *Clinica Chimica Acta*, vol. 55, pp. 307–315 (1974).

Messing et al., "Interstitial Cystitis," *Urology*, vol. 12, No. 4 pp. 381–392 (1978).

Balazs et al., "The Effect of Hyaluronic Acid on Fibroblasts, Mononuclear Phagocytes and Lymphocytes," *Biology of Fibroblasts*, Academic Press, pp. 237–252 (1973).

Kuwahara et al., "Bacterial Infection and Acid Mucopolysaccharides in Epithelium of Rat Urinary Bladder," *Urological Research*, vol. 10, No. 2, pp. 93–96 (1982).

*Primary Examiner*—Shep K. Rose
*Attorney, Agent, or Firm*—Jones & Askew

[57] ABSTRACT

A method of treating cystitis comprising contacting the urinary bladder and associated structures in a mammal having cystitis with a solution containing hyaluronic acid having a average molecular weight of not less than $2 \times 10^5$ Daltons in a concentration effective to treat the cystitis. The solution may further contain an agent effective to treat the associated cause of the cystitis in a concentration effective to treat the associated cause of the cystitis.

7 Claims, 1 Drawing Sheet

% Reduction of Symptoms per Treatment Group at 4, 8, and 12 Weeks

METHOD FOR TREATING THE INTERNAL URINARY BLADDER AND ASSOCIATED STRUCTURES USING HYALURONIC ACID

CROSS-REFERENCE TO RELATED APPLICATIONS

This application is a continuation-in-part of U.S. patent application Ser. No. 08/644,438, filed May 13, 1996, which is a continuation-in-part of U.S. patent application Ser. No. 08/591,015 filed Feb. 8, 1996, abandoned, which is a continuation-in-part of U.S. patent application Ser. No. 08/388,038 filed Feb. 14, 1995, now U.S. Pat. No. 5,591,724.

TECHNICAL FIELD

This relates to urology and pharmacology, and more particularly relates to a method for treating cystitis of the urinary bladder and associated structures in a mammal by contacting the urinary bladder and associated structures with a solution containing hyaluronic acid having an average molecular weight of not less than $2 \times 10^5$ Daltons.

BACKGROUND OF THE INVENTION

In mammals, the unique tight junctions of urinary bladder surface epithelial cells are the fundamental mechanism by which the urinary bladder maintains impermeability. The glycosaminoglycan layer on the luminal surface of the urinary bladder wall may be an important defense mechanism for protecting the transitional epithelium from urinary irritants (Chelsky, M. et al. 1994., *Journal of Urology*, 151:346). This glycosaminoglycan layer consists of mucopolysaccharides attached to a core protein that, in turn, is bound to a central hyaluronic acid string. This highly viscous, highly hydrophilic glycosaminoglycan layer may protect the transitional epithelium of the urinary bladder from irritants in the urine including, but not limited to, pathogens, microcrystals, proteins, calcium and carcinogens (Nickel, J. C. et al. 1993. *Journal of Urology*, 149:716). This glycosaminoglycan layer also may prevent small, uncharged molecules such as urea from diffusing to and across the transitional cell epithelium. Thus, the glycosaminoglycan layer lining the urinary bladder may act as a barrier between the environment within the lumen of the urinary bladder and the transitional epithelium of the urinary bladder, and may protect this transitional epithelium from inflammation, infection, trauma, stone formation and carcinogenesis.

Cystitis is an inflammation of the urinary bladder and associated structures for which there is no universal effective treatment program (Fleischmann, J. D. et al. 1991. *Journal of Urology*, 146:1235). Symptoms resulting from cystitis include, but are not limited to, urgency for urination, increased frequency of urination and suprapubic pain usually relieved by voiding. Other symptoms can include, but are not limited to, arthritis, spastic colon, low grade fever and irritability. Mammals with cystitis can be significantly disabled, and mammals with advanced cystitis can require major surgery in order to function.

Cystitis can result from, among other causes, infection, trauma, allergy, malignancy, uroliths, acute causes and undetermined causes. Infection associated cystitis includes, but is not limited to, inflammation of the urinary bladder and associated structures associated with bacterial, fungal, yeast, viral and parasitic causes. Trauma associated cystitis includes, but is not limited to, inflammation of the urinary bladder and associated structures associated with mechanical, chemical and surgical causes. Mechanical causes include, but are not limited to, cystoscopy, traumatic fibrosis, ultrasound, radiation therapy, catheterization and spinal cord damage. Surgical causes include, but are not limited to, tumor resection, cystotomy, urinary bladder ablation, urethrostomy, and cystocentesis. Allergy associated cystitis includes, but is not limited to, inflammation of the urinary bladder and associated structures associated with hypersensitivity reactions and drug reactions. Acute causes of cystitis includes but are not limited to, inflammation of the urinary bladder and associated structures associated with venereal disease, irritation by a foreign body, injury, and radiation therapy for cancers of the pelvic region. Malignancy associated cystitis includes, but is not limited to, inflammation of the urinary bladder and associated structures associated with cancerous growth. Undetermined causes of cystitis include, but are not limited to, inflammation of the urinary bladder and associated with interstitial cystitis. Other causes of cystitis are known to those skilled in the art and are included as cystitis.

It has been suggested that abnormalities of or deficiencies in the glycosaminoglycan layer lining the transitional epithelium of the urinary bladder may be a primary defect in cystitis. (Eldrup J. 1983. *British Journal of Urology*, 55:488). These abnormalities or deficiencies may enable increased permeability of the transitional epithelium (Parsons, E. L. et al. 1990. *Journal of Urology*, 143:690) and this increased permeability may enable urinary solutes to gain access to the subepithelial tissue and to induce an irritative, inflammatory response that contributes to the symptoms of cystitis.

There is no standard treatment for cystitis. Among the treatments used for interstitial cystitis are hydraulic distention of the urinary bladder, oral amitriptyline or sodium pentosanpolysulfate, intravesical instillation of dimethylsulfoxide, oxychlorosene sodium, silver nitrate, heparin, or a composition comprising an angiostatic steroid and pentosanpolysulfate. However, the efficacy of these treatments is variable.

Hydraulic distention of the urinary bladder is done under general or spinal anesthesia for one to two minutes at a pressure of 80 to 100 cm $H_2O$. In one study using hydraulic distention of the urinary bladder to treat interstitial cystitis, less than 55% of the patients treated reported relief immediately after treatment and only 2% reported relief six months after treatment (Hanno P. M. et al. 1991. *Semen Urology*, 9:143)

Instillation of dimethylsulfoxide (DMSO) into the urinary bladder for six to eight weeks resulted in a 53% response rate to DMSO versus an 18% response rate to placebo, with the average length of response being six months (Perez-Marrero, R. et al. 1967. *Journal of Urology*, 98:671). Pharmacological effects of DMSO include membrane penetration, enhanced drug absorption, anti-inflammatory and analgesic effects, collagen dissolution, muscle relaxation and mast cell histamine release. Side effects include increased vesicle irritability and garlic-like breath odor. Equivalent results to instillation of DMSO have been reported with oxychlorosene sodium (Messing, E. M. et al. 1978. *Urology*, 12:381). However instillation of oxychlorosene sodium requires anesthesia because of intense discomfort.

Sodium pentosanpolysulfate is a low molecular weight synthetic glycosaminoglycan (U.S. Pat. No. 4,524,066 to Wolf) characterized by very low viscosity and high electronegativity. U.S. Pat. No. 4,820,693 to Gillespie (Gillespie '693) discloses a composition and method for arresting angiogenesis and cell, capillary or membrane leakage comprising either oral or intravesical administration of an angiostatic steroid and pentosanpolysulfate. The molecular weight of pentosanpolysulfate is between $1.5 \times 10^3$ and $5 \times 10^3$ Daltons (The Merck Index, 11th Edition. 1989. p. 7093 at 7090). The molecular weight of the pentosanpolysulfate claimed in Gillespie '693 is between $1.6 \times 10^3$ and $6 \times 10^3$ Daltons, and is preferably about $2 \times 10^3$ Daltons. U.S. Pat. No. 4,966,890 to Gillespie (Gillespie '890) discloses a composition and method for treating cystitis comprising either oral or intravesical administration of an angiostatic steroid and pentosanpolysulfate. Gillespie '890 teaches that pentosanpolysulfate can be used in place of heparin and that pentosanpolysulfate, in combination with an angiostatic steroid, cures cystitis by arresting angiogenesis, cell membrane leakage and capillary leakage or exchange in the urinary bladder.

U.S. Pat. No. 5,180,715 to Parsons (Parsons '715) also discloses the use of pentosanpolysulfate for treating cystitis. Parsons '715 provides data to show that oral pentosanpolysulfate at doses in excess of 100 mg per day are most effective for treating cystitis. Parsons '715 teaches that pentosanpolysulfate can be used in place of heparin and that pentosanpolysulfate acts to block bacterial adherence to the transitional epithelium of the urinary bladder.

Pentosanpolysulfate, as disclosed in Gillespie '693, in Gillespie '890 and in Parsons '715, is a low viscosity glycosaminoglycan. As cystitis may be related to a defect in the high viscosity glycosaminoglycan layer on the luminal surface of the urinary bladder, intravesical administration of the low viscosity pentosanpolysulfate does not provide adequate protection to the transitional epithelium of the urinary bladder and associated structures. Therefore, what is needed is a method for the treatment of cystitis that provides adequate protection for the transitional epithelium of the urinary bladder and related structures with minimal adverse side effects.

SUMMARY OF THE INVENTION

A method is provided for treating cystitis in a mammal having cystitis by contacting the transitional epithelium of the internal surface of the urinary bladder and associated structures, which include the renal pelvis, ureters and urethra, of the mammal having cystitis with a solution containing hyaluronic acid having an average molecular weight of not less than $2 \times 10^5$ Daltons in a concentration effective to treat the cystitis.

The hyaluronic acid solution may contain various agents including, but not limited to, antibiotics, bacterial cell extracts, viruses, cytokines, interferons, chemotherapeutics, immunotherapeutics and glycosaminoglycans other than hyaluronic acid.

It is an object of the present invention to provide a method for treating cystitis in a mammal with cystitis by contacting the transitional epithelium of the internal surface of the urinary bladder and associated structures, which include the renal pelvis, ureters and urethra, with a solution containing hyaluronic acid having an average molecular weight of not less than $2 \times 10^5$ Daltons in a concentration effective to treat the cystitis.

It is also an object of the present invention to provide a method for treating cystitis associated with infection, trauma, allergy, malignancy, uroliths, acute causes and undetermined causes by contacting the internal surface of the urinary bladder and associated structures with a solution containing hyaluronic acid having an average molecular weight of not less than $2 \times 10^5$ Daltons in a concentration effective to treat the cystitis associated with infection, trauma, allergy, malignancy, uroliths, acute injuries and undetermined causes.

It is a further object of the present invention to provide a method for treating the cystitis and the associated cause of the cystitis by contacting the internal surface of the urinary bladder and associated structures with a solution containing hyaluronic acid having an average molecular weight of not less than $2 \times 10^5$ Daltons in a concentration effective to treat the cystitis and containing an agent in effective to treat the associated cause of the cystitis in a concentration effective to treat the associated cause of the cystitis.

It is also an object of the present invention to provide a method for treating interstitial cystitis in a mammal with interstitial cystitis by contacting the transitional epithelium of the internal surface of the urinary bladder and associated structures with a solution containing hyaluronic acid having an average molecular weight of not less than $2 \times 10^5$ Daltons in a concentration effective to treat the interstitial cystitis.

It is also an object of the present invention to provide a method for treating cystitis in a mammal which has minimal side effects, is cost efficient, and enables rapid recovery from the treatment.

Other objects, features and advantages of the present invention will become apparent upon reading the following detailed description of the invention when taken in conjunction with the appended claims.

DETAILED DESCRIPTION OF THE INVENTION

As used herein, the phrase "internal surface of the urinary bladder" refers to the transitional epithelium which lines the urinary bladder.

As used herein, the phrase "associated structures" refers to the renal pelvis, ureters and urethra.

As used herein, the phrase "associated cause" refers to cystitis associated with infection, trauma, allergy, malignancy, urolith, acute causes and undetermined causes.

A method is provided for treating cystitis in a mammal with cystitis by contacting the internal surface of the urinary bladder and associated structures with a solution containing hyaluronic acid having an average molecular weight of not less than $2 \times 10^5$ Daltons in a concentration effective to treat the cystitis. Hyaluronic acid is a heteropolysaccharide consisting of alternating residues of D-glucuronic acid and N-acetylglucosamine. Hyaluronic acid is a linear polymer with a molecular weight of up to $13 \times 10^6$ Daltons. It is found in connective tissue, in joint synovial fluid, in ocular vitreous humor, in umbilical cord, in cocks comb and is synthesized by some bacteria including, but not limited to *streptococcal* species. High molecular weight hyaluronic acid inhibits lymphocyte migration (Balazs E. A. et al. 1973. In: *Biology of Fibroblasts*. Academic Press. pp. 237–252). The phagocytic and chemotactic capacities of neutrophils and leukocytes are also inhibited (Brandt, K. D. 1974. *Clinical Chemical Acta* 55:307).

Hyaluronic acid is highly viscous, highly electronegative and highly hydrophilic. The use of hyaluronic acid to treat cystitis in the present method provides unexpectedly excellent results in treating cystitis in a mammal with cystitis. It is believed that hyaluronic acid coats the transitional epithelium of the urinary bladder and associated structures and may provide a barrier between irritants within the lumen of the urinary bladder and associated structures and the transitional epithelium lining the urinary bladder and associated structures.

It has been discovered that hyaluronic acid and salts thereof, having an average molecular weight of not less than $2 \times 10^5$ Daltons, unexpectedly, are successful in treating cystitis in a mammal with cystitis.

The hyaluronic acid in the hyaluronic acid solution employed in the method has an average molecular weight of not less than $2 \times 10^5$ Daltons. Preferably the hyaluronic acid has a molecular weight range of $2 \times 10^5$ to $3.1 \times 10^6$ Daltons. More preferably the hyaluronic acid has molecular weight range of $2 \times 10^5$ to $1.9 \times 10^6$ Daltons. Most preferably the hyaluronic acid has a molecular weight range of $2.5 \times 10^5$ Daltons to $1.2 \times 10^6$ Daltons.

Various methods for obtaining molecular weight fractions of hyaluronic acid are available. These include fractionation of hyaluronic acid prepared from cartilage, fractionation of hyaluronic acid derived from bacteria including, but not limited to, *streptococcal* species, and the purchase of molecular weight fractions of hyaluronic acid from commercial sources including, but not limited to, Fluka Chemical Corporation, Ronkonkoma, N.Y., Genzyme Corporation, Cambridge, Mass. and Lifecore Biomedical, Inc., Chaska, Minn.

The hyaluronic acid for use in the present method is in a concentration from about 0.01 mg/ml to about 50 mg/ml. More preferably the hyaluronic acid is present in a concentration from about 0.1 mg/ml to about 20 mg/ml. Most preferably the hyaluronic acid is present in a concentration from about 0.4 mg/ml to about 2 mg/ml. The hyaluronic acid is solubilized in a pharmaceutically acceptable buffer including, but not limited to, physiological saline and phosphate buffered saline. However, it is to be understood that any of the physiological buffers known to those skilled in the art to be pharmaceutically acceptable for contacting the internal surface of the urinary bladder and associated structures in a mammal can be used in the present method.

The hyaluronic acid solution for use in the present method may further include an antibacterial agent including, but not limited to, aminoglycoside, cephalosporin, gentamycin, macrolide, nitrofurantoin, penicillin, quinolone, sulphonamide, tetracycline, trimethoprim, bacitracin, neomycin, chlorhexidine and mandelamine effective for treating bacterial infection of the bladder and the associated cystitis. Determination of the antibacterial agent and of the amount of the antibacterial agent to be included in the hyaluronic acid solution are well within the determination of those skilled in the art.

The hyaluronic acid solution for use in the present method may further include an antifungal (antiyeast) agent including, but not limited to, amphotericin B and fluconazole effective for treating fungal (yeast) infections of the bladder and associated cystitis. Determination of the antifungal agent and of the amount of the antifungal agent to be included in the hyaluronic acid solution are well within the determination of those skilled in the art.

The hyaluronic acid solution for use in the present invention may further include an immunotherapeutic agent including, but not limited to, bacterial cell extracts, mycobacterial cell wall extracts, live and inactivated *bacillus* Calmette-Guerin (BCG), BCG extracts, cytokines, interferons, interleukins, prostaglandins, and immune stimulants of viral, chemical and molecular biological origin effective for treating immune disorders of the bladder and the associated cystitis. Determination of the immunotherapeutic agent and of the amount of the immunotherapeutic agent to be included in the hyaluronic acid solution are well within the determination of those skilled in the art.

The hyaluronic acid solution for use in the present invention may further include an immunosuppresive agent including, but not limited to, prostaglandins ($PGE_2$) and corticosteroids effective for treating immune disorders of the bladder and the associated cystitis. Determination of the immunosuppresive agent and of the amount of the immunosuppresive agent to be included in the hyaluronic acid solution are well within the determination of those skilled in the art.

The hyaluronic acid solution for use in the present invention may further include a chemotherapeutic agent including, but not limited to, cisplatin, cyclophosphamide, doxorubicin (adriamycin), vincristine, mitomicin-C and thiotepa effective for treating cancer of the bladder and the associated cystitis. Determination of the chemotherapeutic agent and of the amount of the chemotherapeutic agent to be included in the hyaluronic acid solution are well within the determination of those skilled in the art.

The hyaluronic acid solution for use in the present method may further include an anticancer immunotherapeutic agent including, but not limited to, BCG extract, interferon alpha, bacterial cell wall extracts and mycobacterial cell wall extract or other immunotherapeutic agents effective for treating tumors of the bladder and the associated cystitis. Determination of the anticancer immunotherapeutic agent and of the amount of the anticancer immunotherapeutic agent to be included in the hyaluronic acid solution are well within the determination of those skilled in the art.

The hyaluronic acid solution for use in the present method may further include a urolith dissolving agent including, but not limited to, d-penicillamine and pH modifiers effective for treating uroliths of the bladder and the associated cystitis. Determination of the urolith dissolving agent and of the amount of the urolith dissolving agent to be included in the hyaluronic acid solution are well within the determination of those skilled in the art.

The hyaluronic acid solution for use in the present method may further include a pH modifying agent including, but not limited to, sodium acid phosphate and sodium bicarbonate. Determination of the pH modifying agent and of the amount of the pH modifying agent to be included in the hyaluronic acid solution are well within the determination of those skilled in the art.

The hyaluronic acid solution for use in the present method may further include a glycosaminoglycan in addition to hyaluronic acid including, but not limited to, heparin, pentosanpolysulfate, dermatan sulfate, chondroitin sulfate and keratosulfate. Determination of the glycosaminoglycan in addition to hyaluronic acid and of the amount of the glycosaminoglycan in addition to hyaluronic acid to be included in the hyaluronic acid solution are well within the determination of those skilled in the art.

The hyaluronic acid solution for use in the present method is instilled into the urinary bladder and associated structures in a volume of between approximately 1 ml and 200 ml. More preferably, the hyaluronic acid solution is instilled into the urinary bladder and associated structures in a volume of between approximately 20 ml and 150 ml. Most preferably, the hyaluronic acid solution is instilled into the urinary bladder and associated structures in a volume of between approximately 40 ml and 100 ml.

The amount of hyaluronic acid to be instilled into the urinary bladder and associated structures in the present method is between approximately 5 mg and 200 mg. More preferably, the amount of hyaluronic acid to be instilled into the urinary bladder and associated structures is between approximately 25 mg and 100 mg. Most preferably, the amount of hyaluronic acid to be instilled into the urinary bladder and associated structures is between approximately 35 mg and 90 mg.

The hyaluronic acid solution can be administered from a container such as, but not limited to, a bottle or liquid impermeable bag. The hyaluronic acid solution of the present invention can be instilled into the renal pelvis by injection using a needle with attached catheter and allowed to progress down the ureters into the bladder and urethra. The hyaluronic acid solution of the present invention can be instilled into the urinary bladder using a urinary catheter. However, it is to be understood that any method known to those skilled in the art for contacting the internal surface of the urinary bladder and associated structures in a mammal with a pharmaceutical composition can be used in the present invention.

The hyaluronic acid solution should remain in contact with the urinary bladder and associated structures for from approximately 5 minutes to 8 hours. More preferably from 15 minutes to 4 hours. Most preferably from 30 minutes to 2 hours.

Treating cystitis in a mammal having cystitis associated with bacterial infection, viral infection, fungal (yeast) infection, trauma, allergy, malignancy, uroliths, acute causes and undetermined causes by contacting the internal urinary bladder and associated structures with hyaluronic acid and salts thereof, having an average molecular weight of not less than $2 \times 10^5$ Daltons and containing an agent selected from the group consisting of an antibacterial agent, an antifungal (yeast) agent, an immunotherapeutic agent, an immunosuppresive agent, a chemotherapeutic agent, a urolith dissolving agent, a pH modifying agent and a glycosaminoglycan other than hyaluronic acid provides unexpectedly good results in providing relief from the symptoms of the cystitis with minimal adverse side effects.

EXAMPLE 1

Isolation, Purification and Fractionation of Hyaluronic Acid

The following describes a method for the isolation, purification and fractionation of hyaluronic acid from cartilage for use in the cystitis treatment described herein.

Pre-Treatment of Cocks Combs

The preparation of sodium hyaluronate from frozen or fresh cocks combs involves the following steps: The cocks combs are minced, homogenized, dehydrated in acetone, and vacuum dried to a dry powder. The water content of the discarded acetone is less than 2.0%. The powder is digested enzymatically with papain in a buffered aqueous medium containing cysteine hydrochloride. The resulting mixture is clarified and ultrafiltered using a membrane with a molecular weight exclusion limit of $3 \times 10^4$ Daltons. The retained clear liquid has a pH between 5.0 and 7.0. The mucopolysaccharide content is 2.0 and 6.0 mg/ml sodium hyaluronate as determined by glucuronic acid assay. The amino acid content is greater than 6.0 mg/ml as determined by ninhydrin assay.

Complexing, Fractionation, Precipitation

NaCl (up to 0.1M) and cetyl-pyridinium chloride (CPC) are added to the clear liquid with agitation. The precipitate is collected by centrifugation and washed three times in 0.01M NaCl with 0.05% CPC. The precipitate is suspended in 0.05M NaCl with 0.05% CPC with agitation and the cloudy supernatant is eliminated. This procedure is repeated several times using 0.1M NaCl with 0.05% CPC. The precipitate is then dispersed in 0.3M NaCl with 0.05% CPC with agitation and the extraction is repeated three times. The precipitate is then eliminated. The clear supernatants are pooled, brought to 0.23M NaCl, CPC is added, the mixture is treated with Celite®, and filtered. After Celite® treatment, the sodium hyaluronate content is 2.5–5.0 mg/ml as determined by glucuronic acid assay.

Isolation of Hyaluronic Acid

The filtrate is ultrafiltered using a membrane with a molecular weight exclusion limit of $3 \times 10^4$ Daltons and the retained liquid is concentrated. This liquid is precipitated with 95% ethanol and centrifuged. The precipitate is dissolved in 0.1M NaCl and precipitated again with 95% ethanol. The precipitate is collected and washed yielding a crude product having an average molecular weight of not less than $2.5 \times 10^5$ Daltons. The yield is equivalent to 0.6% of original fresh tissue.

Purification of Hyaluronic Acid Fraction

The precipitate is dissolved in pyrogen-free distilled water (10 mg/ml) and ultrafiltered using a membrane with a molecular weight exclusion limit of $2 \times 10^5$ Daltons without addition of supplementary water. This increases the concentration of molecus having a molecular weight greater than $2 \times 10^5$ Daltons. Ultrafiltration is used to reduce the volume to 10% of original volume. Water is added to the concentrated composition and the operation is repeated twice. The concentrated solution is collected and is diluted with water to a concentration of 5 mg/ml hyaluronic acid. NaCl is added to bring the solution to 0.1M and the solution is precipitated with four volumes of 95% ethanol. The precipitate is washed and then vacuum dried.

This purified hyaluronic acid is polydisperse and has an average molecular weight, of not less than $2 \times 10^5$ Daltons. Methods for further fractionating this HA into different molecular weight fractions are well known to those of ordinary skill in this art. Further methods for preparing purified hyaluronic acid of the molecular weights claimed in this invention are disclosed in U.S. Pat. No. 4,141,973 to Balzas which is incorporated by reference.

EXAMPLE 2

Admisistration of Hyaluronic Acid to Five Cystitis Patients

In this pilot study five patients with interstitial cystitis, receive intravesical instillation of 40 mg of hyaluronic acid having an average molecular weight of $6.5 \times 10^5$ Daltons in 40 ml to 70 ml aseptic saline (USP).

Outcome criteria for this pilot study are related to improvement of symptoms based on decreases in pre-therapy symptoms, pre-therapy pain, and pre-therapy urgency.

Subject 1

Patient J M

Interstitial cystitis patient J M (#002) fails treatment with both intravesical heparin instillation and oral pentosan-polysulfate. J M is treated according to the study protocol. Forty mg of hyaluronic acid having an average molecular weight of $6.5 \times 10^5$ Daltons (range $5 \times 10^5$ to $7.3 \times 10^5$ Daltons) in 50 ml of normal saline (USP) is instilled into the urinary bladder under aseptic conditions using a urethral catheter. The catheter is removed and the hyaluronic acid solution is maintained in the urinary bladder for 30 minutes. The treatment is repeated weekly for 7 weeks After the 7th treatment, the patient reports a marked improvement in suprapubic pain and in urgency of urination. The treatment is repeated 4 times during the following 17 weeks. After the last treatment, the patient reports a 100% improvement in suprapubic pain and improvement in urgency. No adverse side effects of the hyaluronic acid treatment are reported by the patient.

Subject 2
Patient G H

Interstitial cystitis patient G H (#003) fails treatment with oral propantheline bromide (2-hydroxyethyl)-diisopropylmethyl ammonium bromide xanthene-9-carboxylate, phenylpropanolamine hydrochloridene and guaifenesin. G H is treated according to the study protocol. Forty mg of hyaluronic acid having an average molecular weight of $6.5 \times 10^5$ Daltons in 50 ml of normal saline (USP) is instilled into the urinary bladder under aseptic conditions using a urethral catheter. The catheter is removed and the hyaluronic acid solution is maintained in the urinary bladder for 60 minutes. The treatment is repeated 4 times during an approximately 12 week period. After the last treatment, the patient reports a 100% improvement in pre-therapy symptoms, pre-therapy pain and pre-therapy urgency. No adverse side effects of the hyaluronic acid treatment are reported by the patient.

Subject 3
Patient L B

Interstitial cystitis patient L B (#001) fails treatment with intravesical infusion of DMSO and heparin. L B is treated according to the study protocol. Forty mg of hyaluronic acid having an average molecular weight of $6.5 \times 10^5$ Daltons in 50 ml of normal saline (USP) is instilled into the urinary bladder under aseptic conditions using a urethral catheter. The catheter is removed and the hyaluronic acid solution is maintained in the urinary bladder for 45 minutes. The treatment is repeated weekly for 5 weeks with significant improvement in pre-therapy symptoms, pre-therapy pain and pre-therapy urgency. Due to an unrelated illness, treatment is interrupted for approximately 7 weeks and symptoms return. After two subsequent treatments, the patient is again improved. Again, due to an unrelated illness, treatment is interrupted for 13 weeks and symptoms return. After two subsequent treatments, the patient reports no improvement in symptoms and treatment is discontinued at the patient's request.

Subject 4
Patient M M

Interstitial cystitis patient M M (#004) is treated according to the study protocol. Forty mg of hyaluronic acid having an average molecular weight of $6.5 \times 10^5$ Daltons in 50 ml of normal saline (USP) is instilled into the urinary bladder under aseptic conditions using a urethral catheter. The catheter is removed and the hyaluronic acid solution is maintained in the urinary bladder for 50 minutes. The treatment is repeated 9 times over a 22 week period. After the last treatment, the patient reports improvement in pre-therapy symptoms, in pre-therapy pain and in pre-therapy urgency. Although the patient reports no side effects from the hyaluronic acid treatment, the patient elects to discontinue hyaluronic acid treatment.

Subject 5
Patient M S

Interstitial cystitis patient M S (#006) is treated according to the study protocol. Forty mg of hyaluronic acid having an average molecular weight of $6.5 \times 10^5$ Daltons in 50 ml of normal saline (USP) is instilled into the urinary bladder under aseptic conditions using a urethral catheter. The catheter is removed and the hyaluronic acid solution is maintained in the urinary bladder for 60 minutes. The treatment is repeated weekly for 7 weeks. At the end of the 7th week there is a marked improvement in pre-therapy symptoms, in pre-therapy pain and in pre-therapy urgency. Four maintenance treatments are given during the following 16 months. Throughout and at the end of each of the maintenance treatments, the marked improvement is maintained.

EXAMPLE 3

Administration of Hyaluronic Acid to Intersistial Cystitis Patients

Hyaluronic acid (HA) is used to treat interstitial cystitis according to the method described herein. Twenty-four humans, each having interstitial cystitis, are treated with hyaluronic acid (sodium hyaluronate) having an average molecular weight of $6.5 \times 10^5$ Daltons.

Inclusion Criteria For This Study Include:
1. $\geq 18$ years of age
2. diagnosis of interstitial cystitis
3. untreated or failure of previous treatment
4. two or more of following findings present: a) suprapubic, urethral, or perineal pain; b) chronic inflammation or mast cell infiltration on cystoscopy or biopsy with no evidence of malignancy; c) hydrodistension under anesthesia to 80 to 100 cm $H_2O$ pressure with glomerulations (multiple petechiae), bloody effluent and diminished urinary bladder capacity; d) aseptic urine cultures; e) decreased compliance on cystometrogram; f) pain on urinary bladder filling (diminished by emptying)

Exclusion Criteria For This Study Include:
1. benign or malignant urinary bladder tumors
2. evidence of vesicoureteral reflux or urethral diverticulum
3. uterine, cervical, vaginal or urethral cancer
4. UTI, vaginitis, prostatitis
5. urinary bladder or lower urethral calculi, active herpes (herpes virus type II)
7. positive urine cytology
8. cystometrogram capacity >400 cc, absence of sensory urgency or unstable urinary bladder
9. waking frequency <5 in 12 hours
10 neurogenic urinary bladder dysfunction
11. patients taking any medication or active treatment for interstitial cystitis treatment within 30 days of enrollment in study
12 prior urinary diversion
13. pregnant women Assessment Criteria For This Study Include:
Pre-treatment symptoms and the effects of HA treatment are assessed using a quality of life symptom score, a visual analog (VAS) pain scale, a visual analog (VAS) urgency scale and a 72 hour voiding record.

Outcome Criteria For This Study Include:
1. Complete Response (CR): Improvement of symptoms with a ≧90% decrease in pre-therapy symptom score, VAS pain scale, VAS urgency scale and patient does not require medication.
2. Partial Response (PR): Incomplete resolution of symptoms with ≧50% decrease in pre-therapy symptom score, VAS pain scale, VAS urgency scale and patient continues to require medication for complete relief of symptoms.
3. Minor Response (MR): Incomplete resolution of symptoms with <50% decrease in pre-therapy symptom score, VAS pain scale, VAS urgency scale and patient continues to require medication for partial relief of symptoms.
4. Failure (F): No improvement in symptoms.
5. Withdrawal (WD): Patient withdraws or is withdrawn from the study.

Treatment Protocols For This Study Include:

Each patient receives intravesical instillation of 40 mg of HA having an average molecular weight of $6.5 \times 10^5$ Daltons in 50 milliliters of normal saline (USP). Under aseptic conditions, a urethral catheter is introduced into the urinary bladder and any residual urine is removed and sent for bacterial culture. Fifty ml of the HA composition is instilled into the urinary bladder and the catheter is removed. The patient is asked to retain the hyaluronic acid solution as long as possible.

The hyaluronic acid instillation is given one time per week for 4 weeks (induction). If the patient's symptoms completely resolve within the 4 week induction period, treatment is given monthly to the end of 12 months (maintenance). If the patient's symptoms partially resolve within the 4 week induction period, the patient is retreated one time per week for 4 weeks. If after retreatment the patient's symptoms completely resolve, maintenance treatment is given. If the patient's symptoms do not resolve at all within the 4 week induction period, treatment is discontinued and the patient is withdrawn from the study.

Results obtained are shown in Table I and in Table II.

Table I shows results from 14 patients entering the study at various times within the study protocol. Twelve of the 14 patients show either a complete response or a partial response to the hyaluronic acid treatment after from 4 to 28 weeks of treatment. Two of the 14 patients show no response to the hyaluronic acid treatment after 8 weeks of treatment.

TABLE I

THERAPEUTIC RESPONSE TO HYALURONIC ACID TREATMENT OF INTERSTITIAL CYSTITIS

| Patient # | Date of 1st Tx (m/d/y) | Week 4 | Week 8 | Week 12 | Week 16 | Week 20 | Week 24 | Week 28 | Week 32 | Week 38 | Week 48 |
|---|---|---|---|---|---|---|---|---|---|---|---|
| 01 | 940615 | CR | PR | PR | CR | CR | CR | CR | | | |
| 02 | 940728 | PR | CR | PR | CR | PR | | | | | |
| 03 | 940802 | | F | PR | PR | | | | | | |
| 04 | 940916 | F | PR | F | PR | | | | | | |
| 06 | 941004 | | F | PR | | | | | | | |
| 07 | 941005 | F | PR | PR | | | | | | | |
| 08 | 941007 | F | PR | | | | | | | | |
| 09 | 941027 | | PR | | | | | | | | |
| 10 | 941026 | PR | PR | CR | | | | | | | |
| 11 | 941106 | F | F | | | | | | | | |
| 12 | 941107 | PR | PR | CR | | | | | | | |
| 13 | 941108 | CR | CR | CR | | | | | | | |
| 14 | 941118 | F | CR | | | | | | | | |
| 15 | 941222 | F | F | | | | | | | | |

Table II shows results for 24 patients completing 24 weeks, 23 patients completing 32 weeks, 20 patients completing 40 weeks, and 16 patients completing 48 weeks of the hyaluronic acid treatment protocol. At the end of the induction period (week 4), 4 patients show a complete response, 10 a partial response, 9 a minor response and 1 no response to the hyaluronic acid treatment. One patient does not complete the induction period. Of the 18 patients remaining in the study after 24 weeks of hyaluronic acid treatment, 6 show a complete response, 6 a partial response, 4 a minor response, and 2 no response. Of the 9 patients remaining in the study after 48 weeks of hyaluronic acid treatment, 2 show a complete response, 6 a partial response and 1 a minor response. Of the 7 patients who withdraw from the study, 3 withdraw for treatment failure and 4 are withdrawn for protocol violations.

TABLE II

RESPONSE RATES TO HYALURONIC ACID (HA) TREATMENT OF INTERSTITIAL CYSTITIS

| Week # | 4 | 8 | 12 | 16 | 20 | 24 | 32 | 40 | 48 |
|---|---|---|---|---|---|---|---|---|---|
| # of Patients | 25 | 24 | 24 | 24 | 24 | 24 | 23 | 20 | 16 |
| CR | 4 (16%) | 4 (17%) | 6 (25%) | 6 (25%) | 6 (25%) | 6 (25%) | 4 (17%) | 4 (20%) | 2 (13%) |
| PR | 10 | 12 | 11 | 11 | 11 | 6 | 8 | 6 | 6 |

TABLE II-continued

RESPONSE RATES TO HYALURONIC ACID (HA)
TREATMENT OF INTERSTITIAL CYSTITIS

| Week # | 4 | 8 | 12 | 16 | 20 | 24 | 32 | 40 | 48 |
|---|---|---|---|---|---|---|---|---|---|
| # of Patients | 25 | 24 | 24 | 24 | 24 | 24 | 23 | 20 | 16 |
| MR | 9 (40%) | 7 (50%) | 5 (46%) | 4 (46%) | 2 (46%) | 4 (25%) | 4 (35%) | 2 (30%) | 1 (37%) |
| F | 1 (36%) | 1 (29%) | 1 (21%) | 1 (17%) | 1 (8%) | 2 (17%) | 0 (17%) | 0 (10%) | 0 (6%) |
| W/D | 1 (4%) | 0 (4%) | 1 (4%) | 2 (4%) | 4 (4%) | 6 (8%) | 7 (0%) | 7 (0%) | 7 (0%) |
|  | (4%) | (0%) | (4%) | (8%) | (17%) | (25%) | (30%) | (35%) | (44%) |

The data in Table I and in Table II demonstrate that contacting the internal urinary bladder with a solution containing hyaluronic acid having an average molecular weight of $6 \times 10^5$ Daltons is unexpectedly effective in relieving the symptoms of interstitial cystitis. That is, the method of treating interstitial cystitis hyaluronic acid described herein results in unexpected and significant improvement in pre-therapy symptoms, pre-therapy pain and pre-therapy urgency.

EXAMPLE 4

Treatment of Intersistial Cystitis with Hylauronic Acid ($1.9 \times 10^6$ Daltons)

An interstitial cystitis patient is treated according to the following protocol. Forty mg of hyaluronic acid having an average molecular weight of $8.7 \times 10^5$ Daltons in 50 ml of normal saline (USP) is instilled into the urinary bladder under aseptic conditions using a urethral catheter. The catheter is removed and the hyaluronic acid solution is maintained in the urinary bladder for 60 minutes. The treatment is repeated weekly and there is a marked improvement in pre-therapy symptoms, in pre-therapy pain and in pre-therapy urgency.

EXAMPLE 5

Treatment of Interstitial Cystitis with Hyaluronic Acid ($1.9 \times 10^6$ Daltons)

An interstitial cystitis patient is treated according to the following protocol. Forty mg of hyaluronic acid having an average molecular weight of approximately $1.9 \times 10^6$ Daltons in 50 ml of normal saline (USP) is instilled into the urinary bladder under aseptic conditions using a urethral catheter. The catheter is removed and the hyaluronic acid solution is maintained in the urinary bladder for 60 minutes. The treatment is repeated weekly and there is a marked improvement in pre-therapy symptoms, in pre-therapy pain and in pre-therapy urgency.

EXAMPLE 6

Treatment of Intersistial Cystitis with Hyaluronic Acid ($6.5 \times 10^5$, $8.7 \times 10^5$ Daltons, and $1.9 \times 10^6$ Daltons)

Hyaluronic acid is used to treat interstitial cystitis in humans having interstitial cystitis according to the present invention. Each patient in this study meets the criteria established by the National Institute of Arthritis, Diabetes, Digestive and Kidney Diseases (NIDDK) for having interstitial cystitis.

Inclusion Criteria For This Study Include:
1. $\geq 18$ years of age
2. diagnosis of interstitial cystitis
3. untreated or failure of previous treatment
4. score of $\geq 6$ on a pre-therapy Symptom Evaluation Score
5. score of $\geq 4$ on a pre-therapy VAS Pain Scale
6. score of $\cong 4$ on a pre-therapy VAS Urgency Scale Exclusion Criteria For This Study Include:
1. urinary bladder capacity >350 cc on awake cystometry
2. duration of symptoms <9 months
3. absence of nocturia
4. symptoms relieved by antimicrobials, urinary antiseptics, anticholinergics or antispasmodics
5. waking frequency <8 in 24 hours
6. bacterial cystitis or prostatitis within a three-month period
7. urinary bladder or lower urethral calculi, active genital herpes
8. uterine, cervical, vaginal or urethral cancer
9. chemical, tuberculous or radiation cystitis
10. benign or malignant urinary bladder tumors
11. neurogenic urinary bladder dysfunction
12. patients taking any medication or active treatment for interstitial cystitis within 30 days of enrollment in study
13. prior urinary diversion
14. pregnant women Assessment Criteria For This Study Include:
Pre-treatment symptoms and the effects of HA treatment are assessed using a quality of life questionnaire, a symptom evaluation score, a visual analog (VAS) pain scale, a visual analog (VAS) urgency scale and a 72 hour voiding record.

Outcome Criteria For This Study Include:
1. Complete Response (CR): Improvement of symptoms with a 75% decrease in pre-therapy symptom evaluation score, pre-therapy VAS pain scale and pre-therapy VAS urgency scale.
2. Partial Response (PR): Incomplete resolution of symptoms and a 50–74.99% decrease in pre-therapy symptom evaluation score, pre-therapy VAS pain scale and pre-therapy VAS urgency scale.
3. Minor Response (MR) Incomplete resolution of symptoms with a <50% decrease in pre-therapy symptom evaluation score, pre-therapy VAS pain scale and pre-therapy VAS urgency scale.
4. Failure (F): No improvement in symptoms.
5. Withdrawal (WD). Patient withdraws or is withdrawn from the study.

Treatment Protocols For This Study Include:

Eleven humans, each having interstitial cystitis, are assigned sequentially to receive intravesical instillations of hyaluronic acid having average an molecular weight of $8.7 \times 10^5$ Daltons (Group A) or $1.9 \times 10^6$ Daltons (Group B). Patients in Group A and in Group B each receive intravesical instillation of 40 mg of the hyaluronic acid of Group A hyaluronic acid or of Group B hyaluronic acid in 50 ml of normal saline (USP). Under aseptic conditions, a urethral catheter is introduced into the urinary bladder and any residual urine is removed and sent for bacterial culture. Fifty ml of the hyaluronic acid composition is instilled into the urinary bladder and the catheter is removed. The patient is asked to retain the hyaluronic acid solution as long as possible.

The hyaluronic acid instillation is given 1 ×/week for 4 weeks (induction) followed by 1×/4 weeks for 8 weeks (maintenance). Therapy is discontinued at 12 weeks after the first hyaluronic acid instillation. The efficacy of hyaluronic acid in the treatment of interstitial cystitis is assessed at 4, 8 and 12 weeks after the first hyaluronic acid instillation using a symptom evaluation score, a VAS pain scale and a VAS urgency scale.

Figure 1:
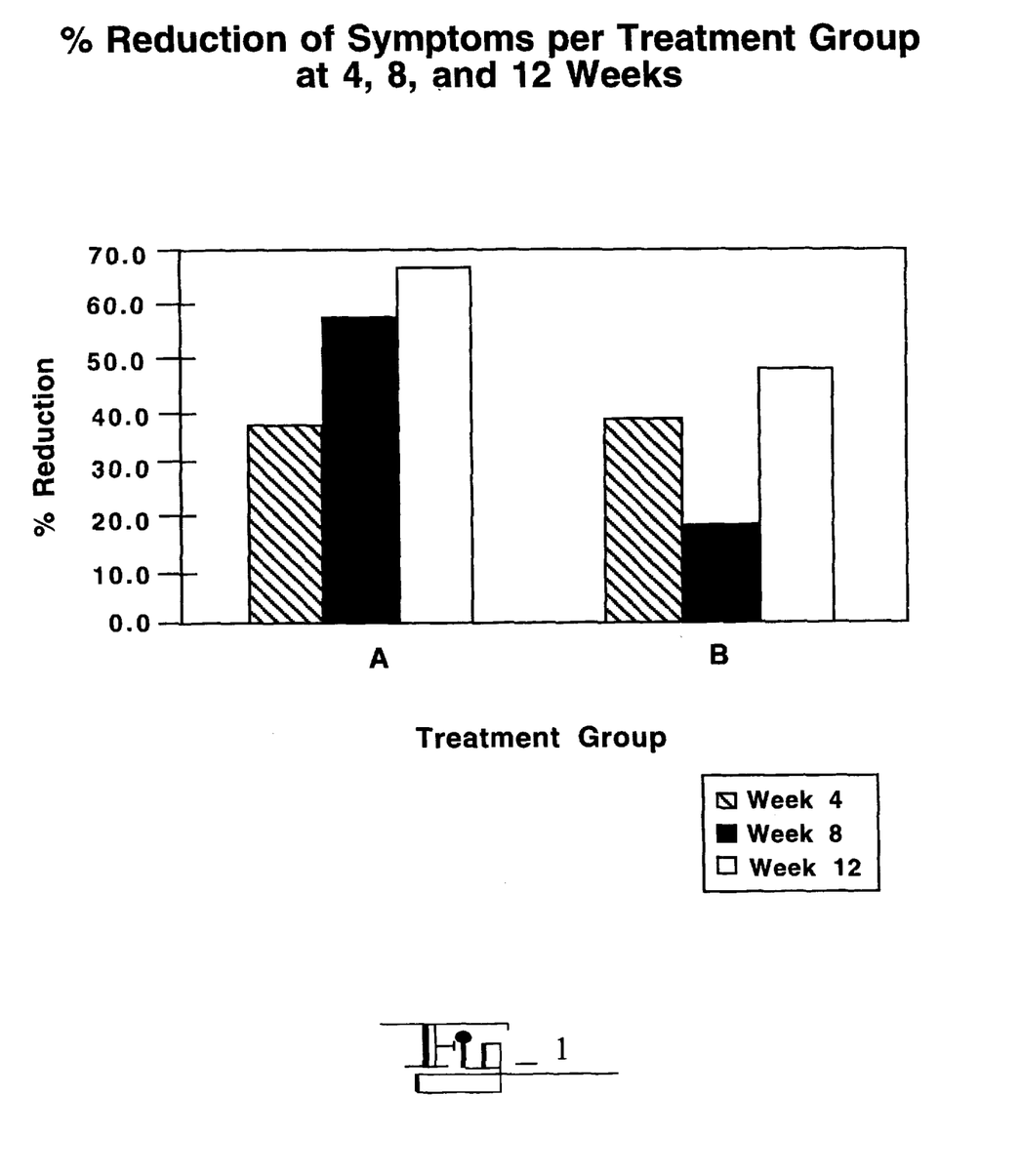
FIG. 1 shows the percent reduction of interstitial cystitis symptoms in Group A and Group B after 4, 8 and 12 weeks of hyaluronic acid treatment.

Results for the 11 patients entering the study at various times within the study period are shown in Table III, Table IV, Table V and FIG. 1.

Table III shows the response of each patient in Group A and in Group B to hyaluronic acid treatment after 4, 8 and 12 weeks. The assessment of response is based on calculating the average of the three scores: symptom evaluation score, VAS pain scale and VAS urgency scale. These data show that hyaluronic acid having average molecular weights of $8.7 \times 10^5$ Daltons (Group A) and of $1.9 \times 10^6$ Daltons (Group B) are effective in relieving the symptoms of interstitial cystitis in a majority of the patients treated.

TABLE III

HYALURONIC ACID TREATMENT OF INTERSTITIAL CYSTITIS

| Patient # | Treatment | Week 4 | Week 8 | Week 12 |
|---|---|---|---|---|
| 1001 | A | MR | CR | CR |
| 1002 | B | F | F | MR |
| 1003 | B | PR | F | PR |
| 2001 | A | MR | MR | MR |
| 2002 | B | PR | PR | PR |
| 2003 | A | F | MR | PR |
| 2004 | B | MR | MR | MR |
| 2005 | A | PR | CR | |
| 2006 | B | PR | MR | |
| 2007 | A | MR | | |
| 2008 | B | MR | | |

Table IV shows the absolute values obtained on the symptom evaluation score (SS), the VAS pain scale (P) and the VAS urgency scale (U) prior to treatment (week 0), at the end of the induction period (week 4) and after weeks 8 and 12 of maintenance treatment. At the end of the 4 week induction period, complete data is available for 11 patients in the study. Of these 11, 4 in group A and 5 in Group B show an improvement in the average % (SS+P+U). One patient in Group A and 1 in Group B show an increase in symptoms after 4 weeks of hyaluronic acid treatment. Of 7 patients completing the 8 week maintenance period (week 12), each shows an improvement in the average % (SS+P+U). Of these 7, 3 are in Group A and 4 are in Group B.

TABLE IV

EVALUATION OF THE EFFICACY OF HYALURONIC ACID IN THE TREATMENT OF INTERSTITIAL CYSTITIS

| Patient # | Week 0 SS | Week 0 P | Week 0 U | Week 4 SS | Week 4 % | Week 4 P | Week 4 % | Week 4 U | Week 4 % | Week 4 Average % (SS + P + U) | Week 6 SS | Week 6 % | Week 6 P | Week 6 % | Week 6 U | Week 6 % | Week 6 Average % (SS + P + U) |
|---|---|---|---|---|---|---|---|---|---|---|---|---|---|---|---|---|---|
| 1001A | 8 | 5.93 | 4.86 | 7 | 13 | 1.46 | 75 | 2.20 | 65 | 48 | 2.00 | 75 | 0.00 | 100 | 0.00 | 100 | 92 |
| 1002B | 8 | 9.46 | 6.06 | 9 | -13 | 8.30 | 12 | 7.13 | -18 | -6 | 9.00 | -13 | 8.30 | 12 | 7.13 | -18 | -6 |
| 1003B | 8 | 4.10 | 4.66 | 6 | 38 | 0.60 | 85 | 0.60 | 87 | 70 | 6.00 | 0 | 4.93 | -20 | 7.23 | -55 | -25 |
| 2001A | 10 | 6.66 | 6.06 | 7 | 30 | 5.50 | 17 | 5.23 | 35 | 28 | 8.00 | 20 | 5.16 | 23 | 4.86 | 40 | 27 |
| 2002B | 10 | 8.26 | 8.66 | 5 | 50 | 2.86 | 65 | 3.30 | 62 | 69 | 4.00 | 60 | 2.13 | 74 | 3.40 | 61 | 65 |
| 2003A | 9 | 7.00 | 5.20 | 7 | 22 | 6.66 | 5 | 7.26 | -40 | -4 | 7.00 | 22 | 4.93 | 30 | 5.03 | 3 | 18 |
| 2004B | 12 | 8.66 | 8.56 | 10 | 17 | 5.93 | 32 | 5.43 | 37 | 28 | 10.00 | 17 | 5.93 | 32 | 5.43 | 37 | 28 |
| 2005A | 6 | 7.00 | 7.93 | 4 | 50 | 1.20 | 83 | 3.16 | 60 | 64 | 1.00 | 88 | 0.00 | 100 | 0.46 | 94 | 94 |
| 2006B | 8 | 5.70 | 7.76 | 5 | 38 | 1.46 | 74 | 3.53 | 55 | 55 | 5.00 | 38 | 5.70 | 0 | 3.63 | 53 | 30 |
| 2007A | 8 | 7.06 | 5.73 | 5 | 38 | 3.06 | 57 | 2.76 | 52 | 49 | | | | | | | |
| 2008B | 9 | 8.20 | 8.20 | 10 | -11 | 7.20 | 12 | 4.93 | 40 | 14 | | | | | | | |

| Patient # | Week 12 SS | % | P | % | U | % | Average % (SS + P + U) |
|---|---|---|---|---|---|---|---|
| 1001A | 2.00 | 75 | 0.03 | 99 | 0.03 | 99 | 91 |
| 1002B | 8.00 | 0 | 0.43 | 95 | 4.81 | 21 | 39 |
| 1003B | 4.00 | 50 | 1.46 | 64 | 1.76 | 62 | 59 |
| 2001A | 6.00 | 40 | 3.86 | 42 | 3.96 | 51 | 44 |
| 2002B | 5.00 | 50 | 1.60 | 81 | 2.33 | 73 | 68 |
| 2003A | 4.00 | 56 | 1.90 | 73 | 1.96 | 62 | 64 |
| 2004B | 7.00 | 42 | 5.93 | 32 | 7.80 | 9 | 27 |
| 2005A | | | | | | | |
| 2006B | | | | | | | |
| 2007A | | | | | | | |
| 2008B | | | | | | | |

(−) values indicate an increase in symptoms.

Table V shows the mean±standard deviation of the percent change from pre-therapy symptoms in the symptom score, the VAS pain scale and the VAS urgency scale for Group A and for Group B patients after 4, 8 and 12 weeks of treatment. Patients in both of the treatment groups, Group A and Group B, show a decrease in pre-therapy symptoms when treated according to the hyaluronic acid method of the present invention.

TABLE V

PERCENT CHANGE FROM BASELINE IN
PATIENT ASSESSMENT BY TREATMENT GROUP

|  |  | A | | | B | | |
|---|---|---|---|---|---|---|---|
|  |  | n | Mean | S.D. | n | Mean | S.D. |
| Symptom Score | Week 4 | 5 | −30.4 | 14.3 | 6 | −19.7 | 26.6 |
|  | Week 8 | 4 | −51.2 | 35.1 | 5 | −20.3 | 29.0 |
|  | Week 12 | 3 | −56.9 | 17.5 | 4 | −35.4 | 23.9 |
| Pain | Week 4 | 5 | 47.2 | 34.7 | 6 | −46.9 | 32.3 |
|  | Week 8 | 4 | −63.0 | 42.8 | 5 | −19.6 | 35.9 |
|  | Week 12 | 3 | −71.5 | 28.8 | 4 | −68.0 | 27.4 |
| Urgency | Week 4 | 5 | −32.4 | 41.4 | 6 | −43.7 | 35.1 |
|  | Week 8 | 4 | −59.3 | 46.2 | 5 | −15.5 | 50.0 |
|  | Week 12 | 3 | −70.9 | 25.4 | 4 | −41.2 | 31.2 |

(−) values indicate a decrease in symptoms.

FIG. 1 shows graphically the percent reduction in pre-therapy symptoms in Group A patients and in Group B patients after 4, 8 and 12 weeks of hyaluronic acid treatment.

The data in Tables I–V and in FIG. 1 demonstrate that, in patients having interstitial cystitis, contacting the urinary bladder with hyaluronic acid according to the present invention results in unexpected and significant improvement in pre-therapy symptoms, in pre-therapy pain and in pre-therapy urgency. These data also show that each of the hyaluronic acid solutions used, $6.5 \times 10^5$ Daltons, $8.7 \times 10^5$ Daltons and $1.9 \times 10^6$ Daltons, are unexpectedly effective in treating interstitial cystitis.

EXAMPLE 7

Hyaluronic Acid Treatment of Bacterial Associated Cystitis

Recently calved dairy heifers, having cystitis associated with bacterial infection as indicated by one or more of the following symptoms: cloudy urine, bloody urine, pyrogen containing urine, bacteria positive urine culture, increased frequency of urination, decreased volume of urine per urination, urine dribbling, decreased food consumption, decreased time spent chewing cud and increased irritability, receive intravesical instillation of hyaluronic acid having an average molecular weight of $6.5 \times 10^5$ Daltons (range $6.0 \times 10^5$ to $1.2 \times 10^6$ Daltons) in an amount effective to treat the cystitis and containing an amount of the antibacterial agent tetracycline effective to treat the bacterial infection. Outcome criteria include improvement of symptoms based on decreases in pre-therapy symptoms and bacteria negative urine culture.

One-hundred and fifty ml of normal saline (USP) containing 80 mg of hyaluronic acid having an average molecular weight of $6.5 \times 10^5$ Daltons and 1000 mg of tetracycline is instilled into the urinary bladder of an anesthetized heifer under aseptic conditions using an appropriate urethral catheter. The catheter is removed and the hyaluronic acid-tetracycline solution is maintained in the urinary bladder for 30 minutes to 2 hours. The treatment is repeated as needed. After treatment, there is a marked improvement in pre-therapy symptoms and a bacteria negative urine culture is obtained. No adverse side effects of the treatment are noted.

EXAMPLE 8

Hyaluronic Acid Treatment of Fungal (Yeast) Associated Cystitis

Animals with cystitis associated with fungal (yeast) infections of the bladder receive intravesical instillation of hyaluronic acid having an average molecular weight of $8.7 \times 10^5$ Daltons in an amount effective to treat the cystitis and containing an amount of the antifungal agent amphotericin B effective to treat the fungal (yeast) infection. Outcome criteria include improvement of symptoms based on decreases in pre-therapy symptoms.

100 ml of normal saline (USP) containing 70 mg of hyaluronic acid having an average molecular weight of $8.7 \times 10^5$ Daltons (range $6.0 \times 10^5$ to $1.2 \times 10^6$ Daltons) and an effective amount of the antifungal agent amphotericin B is instilled into the urinary bladder under aseptic conditions using an appropriate urethral catheter. The catheter is removed and the hyaluronic acid-amphotericin B solution is maintained in the urinary bladder for 30 minutes to 2 hours. The treatment is repeated as needed. After treatment, there is a marked improvement in pre-therapy symptoms. No adverse side effects of the treatment are noted.

EXAMPLE 9

Hyaluronic Acid Treatment of Trauma Associated Cystitis (Irritation)

Patients with cystitis associated with trauma to the bladder causing irritation, of the internal surface of the urinary bladder, receive intravesical instillation of hyaluronic acid having an average molecular weight of $6.5 \times 10^5$ Daltons and containing an amount of the hyaluronic acid effective to treat the cystitis and the irritation. Outcome criteria include improvement of symptoms based on decreases in pre-therapy symptoms.

Fifty ml of normal saline (USP) containing 40 mg of hyaluronic acid having an average molecular weight of $6.5 \times 10^5$ Daltons is instilled into the urinary bladder under aseptic conditions using an appropriate urethral catheter. The catheter is removed and the hyaluronic acid solution is maintained in the urinary bladder for 2 hours. The treatment is repeated as needed. After treatment, a marked improvement in pre-therapy symptoms is noted. No adverse side effects of the treatment are reported.

EXAMPLE 10

Hyaluronic Acid Treatment of Trauma Associated Cystitis (Inflammation)

Patients with cystitis associated with trauma to the bladder causing inflammation to the internal surface of the urinary bladder, receive intravesical instillation of hyaluronic acid having an average molecular weight of $6.5 \times 10^5$ Daltons in an amount effective to treat the cystitis and an amount of the glycosaminoglycan heparin effective to treat the inflammation. Outcome criteria include improvement of symptoms based on decreases in pre-therapy symptoms, pre-therapy pain, and pre-therapy urgency.

Fifty ml of normal saline (USP) containing 40 mg of hyaluronic acid having an average molecular weight of $6.5 \times 10^5$ Daltons and an amount of heparin effective to treat the inflammation is instilled into the urinary bladder under aseptic conditions using an appropriate urethral catheter. The catheter is removed and the hyaluronic acid-heparin solution is maintained in the urinary bladder for 30 minutes to 3 hours. The treatment is repeated as needed. After treatment, a marked improvement in pre-therapy symptoms is noted. No adverse side effects of the treatment are noted.

EXAMPLE 11

Hyaluronic Acid Treatment of Malignancy Associated Cystitis

Patients with cystitis associated with a malignancy of the urinary bladder and associated structures receive intravesical instillation of hyaluronic acid having an average molecular weight of $6.5 \times 10^5$ Daltons in an amount effective to treat the cystitis and containing an amount of the anticancer immunotherapeutic agent mycobacterial cell wall extract preparation (Regressin™, Vetrepharm, Inc., London, Ontario, Canada) effective to treat the malignancy. Outcome criteria include improvement of symptoms based on decreases in pre-therapy symptoms and regression in the malignancy as indicated by urinary cytology.

Fifty ml of normal saline (USP) containing 40 mg of hyaluronic acid having an average molecular weight of $6.5 \times 10^5$ Daltons and 4 mg of the anticancer immunotherapeutic agent mycobacterial cell wall (Regressin™) is instilled into the urinary bladder under aseptic conditions using a urethral catheter. The catheter is removed and the hyaluronic acid-mycobacterial cell wall solution is maintained in the urinary bladder for 30 minutes to 2 hours. The treatment is repeated as needed. After treatment, there is a marked improvement in pre-therapy symptoms and urinary cytological examination is negative for cancerous and pre-cancerous cells. No adverse side effects of the treatment are reported.

EXAMPLE 12

Hylauronic Acid Treatment of Malignancy Associated Cystitis (Discreet Malignant Tumors)

Patients with cystitis associated with discrete malignant tumor(s) of the urinary bladder receive intravesical instillation of hyaluronic acid having an average molecular weight of $6.5 \times 10^5$ Daltons in an amount effective to treat the cystitis and containing an amount of the anticancer immunotherapeutic agent thiotepa effective to treat the tumor(s). Outcome criteria include improvement of symptoms based on decreases in pre-therapy symptoms and a regression in the tumor(s) as indicated by biopsy.

Fifty ml of normal saline (USP) containing 40 mg of hyaluronic acid having an average molecular weight of $6.5 \times 10^5$ Daltons and an amount of the anticancer immunotherapeutic agent thiotepa effective to treat the tumors is instilled into the urinary bladder under aseptic conditions using a urethral catheter. The catheter is removed and the hyaluronic acid-thiotepa solution is maintained in the urinary bladder for 30 minutes to 4 hours. The treatment is repeated as needed. After treatment, there is a marked improvement in pre-therapy symptoms and tumor biopsy indicates regression of the tumor(s). No adverse side effects of the treatment are noted.

EXAMPLE 13

Hyaluronic Acid Treatment of Urolith Assoicated Cysitits

Neutered male cats having cystitis associated with Sistine crystaluria and urethral blockage (feline urinary syndrome) as indicated by one or more of the following symptoms: crystaluria, cloudy urine, bloody urine, blood clots in urine, decreased frequency of urination, decreased volume of urine per urination, decreased food consumption and increased irritability, receive intravesical instillation of hyaluronic acid having an average molecular weight of $6.5 \times 10^5$ Daltons in an amount effective to treat the feline urinary syndrome. Outcome criteria include decreased crystaluria, relief of urethral blockage, increased frequency and volume of urination, increased food consumption and decreased irritability.

A cat is anesthetized or tranquilized and 10 ml of normal saline (USP) containing 8 mg of hyaluronic acid having an average molecular weight of $6.5 \times 10^5$ Daltons is instilled into the urinary bladder under aseptic conditions using an appropriate urethral catheter. The catheter is removed and the solution is maintained in the urinary bladder for 30 minutes to 2 hours. The treatment is repeated as needed. After treatment, the cat urinates normally and is clinically negative for symptoms of feline urinary syndrome. No adverse side effects of the treatment are reported.

EXAMPLE 14

Hyaluronic Acid Treatment of Urolith Associated Cystitis

Neutered male cats having cystitis associated with crystaluria and urethral blockage (feline urinary syndrome) as indicated by one or more of the following symptoms: crystaluria, cloudy urine, bloody urine, blood clots in urine, decreased frequency of urination, decreased volume of urine per urination, decreased food consumption and increased irritability, receive intravesical instillation of hyaluronic acid having an average molecular weight of $6.5 \times 10^5$ Daltons in an amount effective to treat the cystitis and containing an amount of the urolith dissolving agent d-penicillamine effective to dissolve the uroliths. Outcome criteria include decreased crystaluria, relief of urethral blockage, increased frequency and volume of urination, increased food consumption and decreased irritability.

A cat is anesthetized or tranquilized and 10 ml of normal saline (USP) containing 8 mg of hyaluronic acid having an average molecular weight of $8.7 \times 10^5$ Daltons and containing an effective amount of d-penicillamine is instilled into the urinary bladder under aseptic conditions using an appropriate urethral catheter. The catheter is removed and the solution is maintained in the urinary bladder for 30 minutes to 2 hours. The treatment is repeated as needed. After treatment, the cat urinates normally and is clinically negative for symptoms of feline urinary syndrome. No adverse side effects of the treatment are reported.

Although the invention has been described in reference to particular means, materials and examples, it is to be understood that the invention is not limited to the particulars disclosed and extends to all equivalents within the scope of the claims.

We claim:

1. A method of treating cystitis comprising the step of contacting the epithelium of the internal urinary bladder and associated structures in a mammal having cystitis with a solution containing hyaluronic acid having an average molecular weight of not less than $2 \times 10^5$ Daltons in a concentration from about 0.01 mg/ml to about 25 mg/ml in a volume from about 5 ml to about 200 ml effective to treat the cystitis.

2. The method of claim 1, wherein the hyaluronic acid has a molecular weight range of $5 \times 10^5$ to $3.1 \times 10^6$ Daltons.

3. The method of claim 2, wherein the hyaluronic acid has a molecular weight range of $6 \times 10^5$ to $1.2 \times 10^6$ Daltons.

4. The method of claim 3, wherein the hyaluronic acid has an average molecular weight of $6.5 \times 10^5$ Daltons.

5. The method of claim 3, wherein the hyaluronic acid has an average molecular weight of $8.7 \times 10^5$ Daltons.

6. The method of claim 2, wherein the hyaluronic acid has a molecular weight range of $1.2 \times 10^6$ to $3.1 \times 10^6$ Daltons.

7. The method of claim 6, wherein the hyaluronic acid has an average molecular weight of $1.9 \times 10^6$ Daltons.

* * * * *